United States Patent
Christensen

(10) Patent No.: US 9,907,933 B2
(45) Date of Patent: Mar. 6, 2018

(54) SUPPORT DEVICE

(71) Applicant: Lynda D Christensen, Austin, TX (US)

(72) Inventor: Lynda D Christensen, Austin, TX (US)

(*) Notice: Subject to any disclaimer, the term of this patent is extended or adjusted under 35 U.S.C. 154(b) by 321 days.

(21) Appl. No.: 14/717,907

(22) Filed: May 20, 2015

(65) Prior Publication Data
US 2015/0343185 A1 Dec. 3, 2015

Related U.S. Application Data

(60) Provisional application No. 62/007,144, filed on Jun. 3, 2014.

(51) Int. Cl.
*A61M 27/00* (2006.01)
*A61M 25/02* (2006.01)
*A61M 1/00* (2006.01)

(52) U.S. Cl.
CPC ............ *A61M 25/02* (2013.01); *A61M 1/008* (2013.01); *A61M 2025/0206* (2013.01); *A61M 2209/088* (2013.01)

(58) Field of Classification Search
CPC ...... A61M 27/00; A61M 25/02; A61M 1/008; A61M 2209/088; A61M 2025/0206; A61M 2025/0253; A61M 2025/026; A61F 5/4408; A41D 27/20; A41D 27/201; A41D 27/202; A41D 27/204; A41D 27/205; A41F 9/002; A41F 9/007; A41F 15/00; A41F 15/002; A45C 2007/0009; A45F 3/02; A45F 2005/006; A45F 2003/148; Y10S 2/92
See application file for complete search history.

(56) References Cited

U.S. PATENT DOCUMENTS

| | | | | |
|---|---|---|---|---|
| 1,405,744 A | * | 2/1922 | Sampliner | A41D 23/00 2/91 |
| 2,462,727 A | * | 2/1949 | Danelz | A41D 25/00 2/207 |
| 3,152,339 A | * | 10/1964 | Conville | A41D 27/20 2/250 |
| 3,197,099 A | * | 7/1965 | Doba | A45F 5/00 224/148.4 |
| 3,749,237 A | * | 7/1973 | Dorton | A61F 13/20 206/390 |

(Continued)

*Primary Examiner* — Adam Marcetich
(74) *Attorney, Agent, or Firm* — Law Offices of Mark L. Berrier

(57) ABSTRACT

Systems and methods for securely supporting devices such as reservoirs for surgical drains or catheters. In one embodiment, a surgical drain support apparatus comprises a sash having a first end and a second end. The sash has an opening such as a slit or a loop at the second end. When the first end is inserted through the opening, the sash forms an adjustable loop that is placed around a user's body (e.g., over the shoulder or around the waist), thereby supporting the apparatus on the user's body. The first end of the sash, which hangs downward from the large loop, has one or more compartments that hold surgical drain reservoirs. The first end of the sash also has a strap attached to it that can be wrapped around the user's body (e.g., around the leg) to hold the first end of the sash against the user's body.

14 Claims, 4 Drawing Sheets

(56) References Cited

U.S. PATENT DOCUMENTS

| | | | | |
|---|---|---|---|---|
| 3,796,357 | A * | 3/1974 | Johnson | A45F 3/02 224/602 |
| 3,935,597 | A * | 2/1976 | Frechmann | A41D 23/00 2/207 |
| 4,666,432 | A * | 5/1987 | McNeish | A61M 25/02 128/DIG. 26 |
| 4,710,983 | A | 8/1987 | Markoff | |
| 4,955,516 | A * | 9/1990 | Satterfield | B62J 9/005 224/414 |
| 5,443,576 | A * | 8/1995 | Hauter | A63B 69/0086 273/DIG. 19 |
| 5,520,462 | A * | 5/1996 | Clark | G10G 7/005 190/102 |
| 5,529,228 | A * | 6/1996 | Biagi | A45F 3/14 224/148.5 |
| 5,692,604 | A * | 12/1997 | Houk | A45C 3/004 190/111 |
| 5,947,241 | A * | 9/1999 | Rausch | A45C 13/00 150/111 |
| 6,206,854 | B1 * | 3/2001 | Weaver | A41D 13/1245 128/DIG. 26 |
| 6,332,222 | B1 * | 12/2001 | Graham | A41D 3/00 2/69 |
| 7,927,311 | B1 * | 4/2011 | Bachelder | A45F 5/00 224/148.4 |
| 9,089,198 | B1 * | 7/2015 | Devereaux | A45F 5/022 |
| 2003/0183313 | A1 * | 10/2003 | Rushlow | A45C 1/04 150/134 |
| 2004/0088778 | A1 * | 5/2004 | Adler | A41D 15/00 2/279 |
| 2006/0266452 | A1 * | 11/2006 | Huie | A45C 13/08 150/105 |
| 2007/0022518 | A1 * | 2/2007 | Sheu | A41D 23/00 2/207 |
| 2007/0116384 | A1 * | 5/2007 | Mason | A45C 3/12 383/9 |
| 2008/0011800 | A1 * | 1/2008 | Vandevere | A45F 3/14 224/625 |
| 2009/0052809 | A1 * | 2/2009 | Sampson | B65D 81/389 383/38 |
| 2010/0235963 | A1 | 9/2010 | Haydon | |
| 2010/0235966 | A1 * | 9/2010 | DeHart | A41D 27/20 2/252 |
| 2011/0016615 | A1 * | 1/2011 | Massey | A41D 27/201 2/251 |
| 2011/0174824 | A1 * | 7/2011 | Potts | A45C 7/0077 220/531 |
| 2012/0079644 | A1 * | 4/2012 | Benderradji | A41D 23/00 2/207 |
| 2012/0091181 | A1 | 4/2012 | Barnes | |
| 2013/0245584 | A1 | 9/2013 | Krasikoff | |
| 2013/0269587 | A1 * | 10/2013 | Greene | B63B 17/00 114/343 |
| 2013/0296814 | A1 | 11/2013 | Antholz | |
| 2015/0137672 | A1 * | 5/2015 | Caskenette | A47F 7/146 312/188 |
| 2015/0157490 | A1 * | 6/2015 | Wellborn | A61F 5/4408 604/345 |

* cited by examiner

SUPPORT DEVICE

CROSS-REFERENCE TO RELATED APPLICATIONS

This application claims the benefit of U.S. Provisional Patent Application No. 62/007,144, by Lynda D. Christensen, filed Jun. 3, 2014, which is incorporated by reference as if set forth herein in its entirety.

BACKGROUND

Field of the Invention

The invention relates generally to devices for supporting surgical drains or catheters in a manner that allows them to be secured to a patient's body, thereby preventing the surgical drains or catheters from being pulled loose from their points of attachment to a person's body.

Related Art

In some instances, after surgical a procedure is performed on a patient, or after placement of a catheter in a patient, it is necessary to provide a device to assist in the removal of fluids from the patient's body. This is especially true in the case of surgical procedures that involve the removal of tissue, such as mastectomies or lumpectomies. The use of a surgical drain allows the fluids to exit the patient's body, thereby reducing swelling and infection that may result from the presence of the fluids in the body. It may be necessary to use more than one surgical drain, depending upon the circumstances of a particular case.

A surgical drain typically includes a drainage tube that extends from the surgical field within the patient's body, through the surrounding tissue, exiting the body through a surgical incision. Fluid that accumulates within the patient's body flows into a first end of the drainage tube that is positioned within the surgical field. The fluid flows through the drainage tube and into a reservoir that is attached to the second end of the drainage tube. Commonly, the reservoir is a flexible vacuum bulb that maintains a slight vacuum within the drainage tube and thereby facilitates the flow of fluids from the body, through the drainage tube and into the reservoir. Depending upon the amount of fluid that is expected to be accumulated, it may be necessary to use multiple surgical drains to remove the fluid.

The drainage tube is commonly attached to the body with one or more stitches near the surgical incision through which the drainage tube exits the patient's body. This is intended to help secure the drainage tube and to help prevent it from being pulled out of the patient's body. This arrangement is, however, very delicate, and it is not uncommon for these stitches to be pulled loose by an unsecured fluid reservoir. It is therefore important to provide support for the surgical drain (particularly the fluid reservoir) in order to prevent the stitches and/or the surgical drain from being pulled out of the patient's body.

The drainage reservoirs typically have a small piece of material (e.g., a loop) which extends from the reservoir to allow it to be supported. Conventionally, this loop of material is attached to the patient's clothing (a gown, for example) by a safety pin. While this does allow the drainage reservoir to be supported somewhat, the drainage reservoir may still move quite a bit, particularly when the reservoir is pinned to the type of open gown that is commonly worn by a patient in a hospital environment. It is not unusual for the drainage reservoir to be able to move sufficiently to tug on the drainage tube, causing discomfort to the patient and possibly tearing the stitches and/or pulling the tube from the patient's body.

The pinning of the drainage reservoir to the patient's clothing may also be an unsatisfactory solution in some situations, such as when the patient needs to take a shower. Obviously, it would be difficult for the patient to clean himself or herself while wearing a hospital gown in the shower. Often, patients are expected to simply hold the drainage reservoirs while they clean themselves. Showering with only one hand is clearly awkward and inefficient, and may also be dangerous if the patient slips or needs to support himself/herself in the shower.

It would therefore be desirable to provide improved means for supporting drain reservoirs so that the comfort and safety of the patient is improved.

SUMMARY OF THE INVENTION

This disclosure is directed to systems and methods for securely supporting devices such as reservoirs for surgical drains or catheters that solve one or more of the problems discussed above. In one particular embodiment, a surgical drain support apparatus comprises a sash having a first end and a second end. The sash has an opening (e.g., a slit or a loop) at the second end. When the first end is inserted through the opening, the sash forms an adjustable loop that can be placed around a user's body (e.g., over the shoulder or around the waist), thereby supporting the apparatus on the user's body. The first end of the sash, which hangs downward from the large loop, has one or more compartments that hold surgical drain reservoirs. The first end of the sash also has a strap attached to it. The strap can be wrapped around the user's body (e.g., around the leg) to hold the first end of the sash against the user's body.

In one embodiment, the sash is a strip of fabric. The fabric may be any suitable type of fabric, and may be selected for its softness, absorbency, ease of cleaning, or other characteristics. The strip of fabric may have a tubular structure that is laid flat. The compartments for the drainage reservoirs may be formed by attaching them to the sash (e.g., by sewing pockets onto the fabric strip), or they may be formed in the sash itself (e.g., by enclosing a portion of the tubular structure and forming an opening such as a slit in the enclosed portion so that a drainage reservoir can be inserted into it). Fasteners may be provided at the openings to the compartments to allow them to be closed, thereby preventing the drainage reservoirs from falling out of the compartments. Fasteners may also be provided to segregate larger compartments (suitable for larger reservoirs) into smaller compartments (suitable for smaller reservoirs).

An expansion component may be attached to the sash to provide the capability of supporting additional drainage reservoirs. In one embodiment, the expansion component is a rectangular piece of fabric that has pockets at opposing ends (where the ends are the smaller sides of the rectangle). The openings of the pockets face toward each other (i.e., toward the center of the piece of fabric) so that when the fabric is folded in half, the openings face upward. The expansion component can be installed in the opening in the end of the sash and secured with fasteners so that the pockets of the expansion component can be used to support additional drainage reservoirs. The expansion component can alternatively be installed on a horizontally extending member of a walker, bedrail, chair, or the like and used to store cell phones, wallets or similarly sized items.

Alternative embodiments may include methods of making and/or using the surgical drain support apparatus. Numerous other embodiments may also be possible.

BRIEF DESCRIPTION OF THE DRAWINGS

Other objects and advantages of the invention may become apparent upon reading the following detailed description and upon reference to the accompanying drawings.

Figure 1:
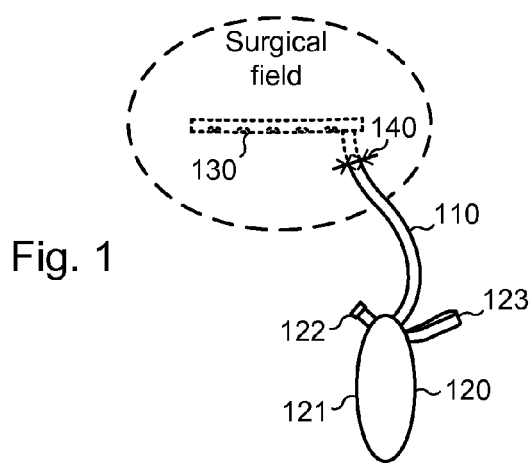
FIG. 1 is a diagram illustrating the structure of an exemplary surgical drain.

While the invention is subject to various modifications and alternative forms, specific embodiments thereof are shown by way of example in the drawings and the accompanying detailed description. It should be understood, however, that the drawings and detailed description are not intended to limit the invention to the particular embodiment which is described. This disclosure is instead intended to cover all modifications, equivalents and alternatives falling within the scope of the present invention as defined by the appended claims. Further, the drawings may not be to scale, and may exaggerate one or more components in order to facilitate an understanding of the various features described herein.

DETAILED DESCRIPTION OF EXEMPLARY EMBODIMENTS

One or more embodiments of the invention are described below. It should be noted that these and any other embodiments described below are exemplary and are intended to be illustrative of the invention rather than limiting.

As described herein, various embodiments of the invention comprise systems and methods for securely supporting devices such as reservoirs for surgical drains or catheters. Embodiments of the present invention provide improved means for supporting these reservoirs, wherein the reservoirs are supported and held securely in position against the patient's body without the need for the patient to hold the reservoirs himself/herself. It should be noted that, while embodiments of the invention which are disclosed herein are described primarily in relation to the support of surgical drain reservoirs, they may be used to support other items as well. These items may include medical items, such as surgical drain or catheter reservoirs, or non-medical items, such as cell phones, wallets, etc.

In one embodiment, the surgical drain support device includes an elongated body formed by a material such as a strip of fabric that has, at a first end, one or more pockets suitable for holding surgical drains. At the second, opposite end of the strip of fabric, there is a hole or loop through which the first end can be inserted. When the second end (the pocket-end) of the fabric has been inserted through the first end (the hole-end), the strip forms a large loop that can be positioned around the patient's body. For instance, the large loop can be placed over the patient's shoulder, similar to a sash, or around the patient's waist. The pocket-end of the fabric strip hangs downward from the larger loop, so that the surgical drains which are placed in the pockets are supported by the larger loop around the patient's body. A ribbon or strap that is connected to the pocket-end of the fabric strip is then wrapped around the patient's body in order to hold this end of the fabric strip (and consequently the drainage reservoirs) against the patient's body. This prevents the reservoirs from swinging outward from the body and tugging on the drainage tubes, which could result in tearing of the patient's stitches, or pulling the drainage tube from the patient's body. This exemplary embodiment and others will be described in more detail below.

Referring to FIG. 1, a diagram illustrating the structure of an exemplary surgical drain is shown. As depicted in this figure, a surgical drain consists of a drainage tube 110, a lower end of which is connected to a drainage reservoir 120. The upper end of drainage tube 110 may be connected to a second tube 130 which as a number of perforations therein. The perforations allow fluid to be drained from the multiple locations of the perforations, rather than from the single opening at the upper end of drainage tube 110.

The upper end of drainage tube 110 (and or second tube 130) is positioned within the surgical field in the patient's body at the end of the patient's surgery. Drainage tube 110 extends from this location within the patient's body, through a surgical incision 140, to the exterior of the patient's body. Surgical incision 140 is then closed, and one or more stitches are used to secure drainage tube 110 the patient's body. Drainage reservoir 120 is then connected to the lower end of drainage tube 110. In this case, drainage reservoir 120 is a vacuum-type reservoir having a flexible body 121. Body 121 can be squeezed to expel air from the reservoir, and then released so that it attempts to return to its original shape, reducing the air pressure within the reservoir and drawing fluid from the drainage tube. A valve or capped tube 122 is provided to allow the air to be expelled from the reservoir to create the reduced pressure inside the reservoir. A small strap 123 is also provided on the upper end of drainage reservoir 120. Strap 123 is conventionally used to attach the drainage reservoir to a patient's hospital gown or other clothing (e.g., with a safety pin).

Figure 2A:
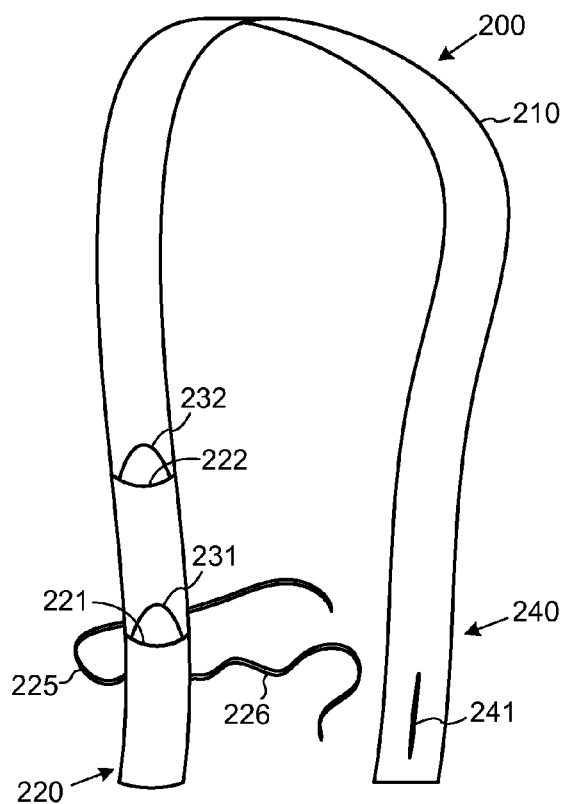
FIGS. 2A and 2B are diagrams illustrating a surgical drain support device in accordance with one embodiment.
Figure 2B:
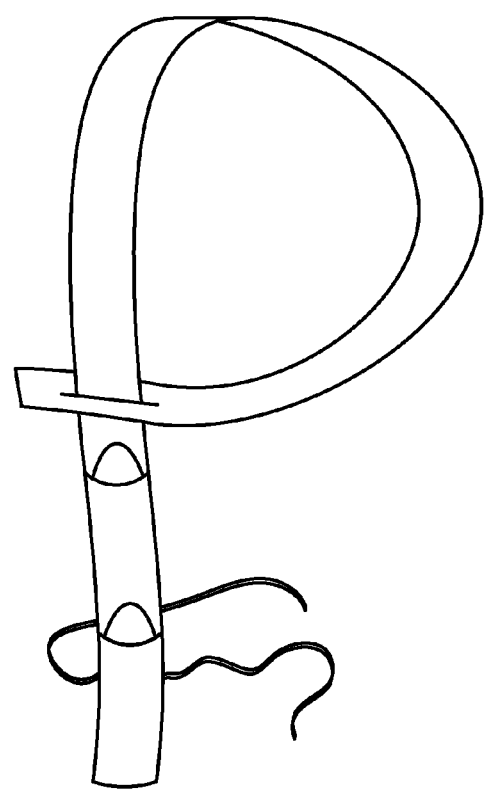

Referring to FIGS. 2A and 2B, a support device in accordance with one embodiment is shown. The device has an elongated body or sash 210, which in this embodiment is a strip of fabric. Various different types of fabric may be used, depending upon the particular characteristics that are desired. For example, it may be desirable to use a fabric such as a pliable, flexible, non-absorbent plastic mesh that is suitable for use in a shower environment and can be easily cleaned. In another instance, it may be desirable to use a fabric that is soft and suitable for use in a generally dry environment, but may be absorbent, so that leaks from the drainage reservoirs may be absorbed or contained. Other fabrics, such as a lycra (elastin) fabric or similar "performance" fabrics that are both soft/absorbent and easily cleaned may also be used. Fabric strip 210 may be any suitable length, but in one embodiment is approximately 4-5 feet long.

It should be noted that, while the present devices may be worn in various different ways, including over the shoulder or around the waist, it may be convenient to refer to the elongated body of the device that forms the loop around the user's body as a sash. Thus, references to the device having a sash should not be construed to limit its use to any particular position on the body (e.g., over the shoulder).

Figure 3:
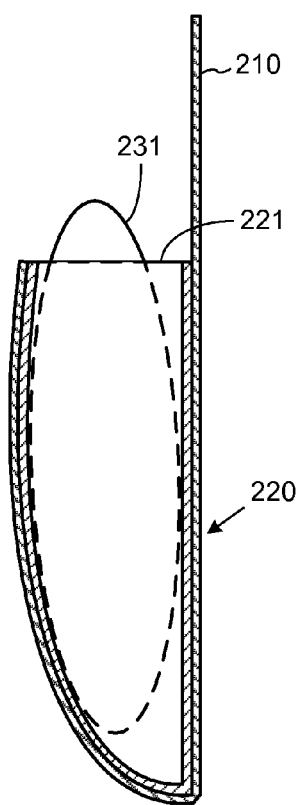
FIG. 3 is a diagram illustrating a pocket in a surgical drain support device for holding a drainage reservoir in accordance with one embodiment.

One end 220 of fabric strip 210 has one or more compartments or pockets 221, 222. Each of the pockets is designed to hold a corresponding drainage reservoir (231, 232). FIG. 3 shows an enlarged view of a drainage reservoir 231 contained in the corresponding pocket 221 at the end of fabric strip 210. (Although not shown in this figure, a drainage tube will be connected to the drainage reservoir when in use.) Drainage reservoirs may have different sizes, so the pockets may be sized accordingly. For instance, in one embodiment, fabric strip 210 and pockets 221, 222 may have a narrower design to hold smaller drainage reservoirs, while in another embodiment, the fabric strip and pockets may have a wider design to accommodate larger drainage reservoirs. In still other embodiments, snaps or other fasteners are provided to enable the segregation of larger pockets into smaller pockets. The depth of each pocket and the number of pockets that are incorporated into the fabric strip may vary from one embodiment to another. In the example of FIG. 3, a liner 310 is provided on the interior of pocket 221. Liner 310 may be liquid impermeable, so that fluids which may leak out of drainage reservoir 231 are contained within the pocket, or it may be absorbent, so that leaked fluids are absorbed by the liner. The liner may be removable to facilitate cleaning.

A second end 240 of fabric strip 210 has an opening 241 in it. As depicted in FIGS. 2A and 2B, opening 241 is a simple slit in the fabric strip. In alternative embodiments, the opening may be formed in a different manner, such as by attaching a fabric loop to the end of fabric strip 210. Other alternatives may also be suitable. Opening 241 in the second end of the fabric strip is large enough to allow the first end (220) of the fabric strip to be positioned through the opening. This forms fabric strip 210 into a loop (as shown in FIG. 2B) from which first end 220 extends.

Figure 4:
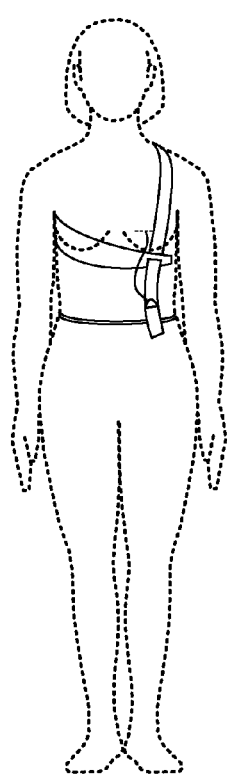
FIG. 4 is a diagram illustrating the manner in which a surgical drain support device can be worn over the shoulder of a patient in accordance with one embodiment.
Figure 5:
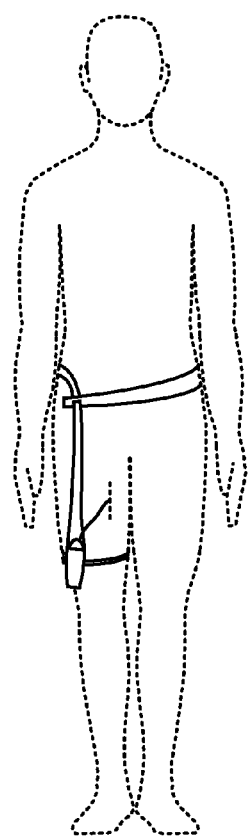
FIG. 5 is a diagram illustrating the manner in which a surgical drain support device can be worn around the waist of a patient in accordance with one embodiment.

Loop 250 which is formed by fabric strip 210 is positioned around the patient's body with the first end 220 extending downward. If the patient has had surgery on the upper part of the body, the loop of fabric strip 210 can be placed over one shoulder and across the torso in the same manner as a sash (see, e.g., FIG. 4). If the patient has had surgery on the lower part of the body, it may be more convenient to place the loop of fabric strip 210 around the patient's waist similar to a belt as shown in FIG. 5. In either case, first end 220 will extend downward, below the incision through which the drainage tube enters the patient's body. The drainage reservoir attached to the drainage tube is placed in one of the pockets in the first end 220 of the fabric strip 210.

The first end 220 of fabric strip 210 has a strap (225, 226) attached to it to allow the first end to be secured to the patient's body. The strap may be made of ribbon, elastic or any other suitable material. As depicted in FIG. 2, the strap includes two ribbons that are attached to first end 220. The ribbons are long enough that they can be wrapped around the patient's body (for example, the torso as shown in FIG. 4, or the leg as shown in FIG. 5) and tied together. In alternative embodiments, the straps may be connected using snaps, hook-and-loop fasteners, or other means. The strap may be adjustable so that it can be shortened or lengthened.

In one embodiment, the device may be designed specifically for a patient who has had a mastectomy or lumpectomy. In this embodiment, the strip of fabric may be worn across the patient's torso, over the breast (as illustrated in FIG. 4), thereby providing support to the breast. The portion of the fabric strip that supports the breast may be widened, or may include additional structure to provide more support for the patient's breast. It may be preferred to use a softer fabric for this portion of the fabric strip, or portions that may contact sensitive areas of the patient's body (e.g., near a surgical incision). The more comfortable fabric may, for example, be layered over the base fabric strip, or the fabric strip may have different sections that use different materials.

Figure 6:
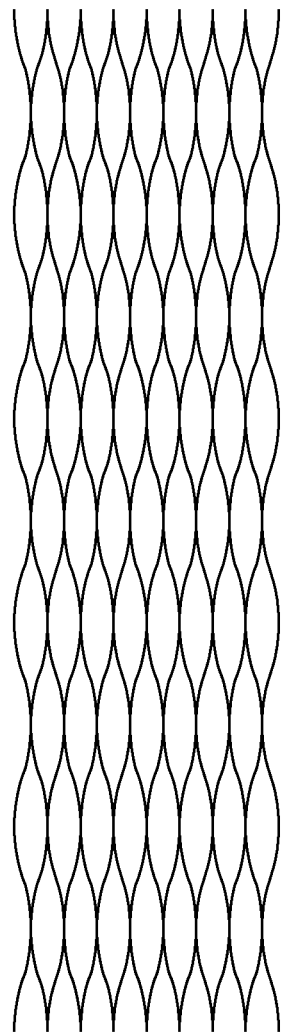
FIG. 6 is a diagram illustrating a plastic mesh that can be used to form the elongated body of a surgical drain support device in accordance with one embodiment.
Figure 7:
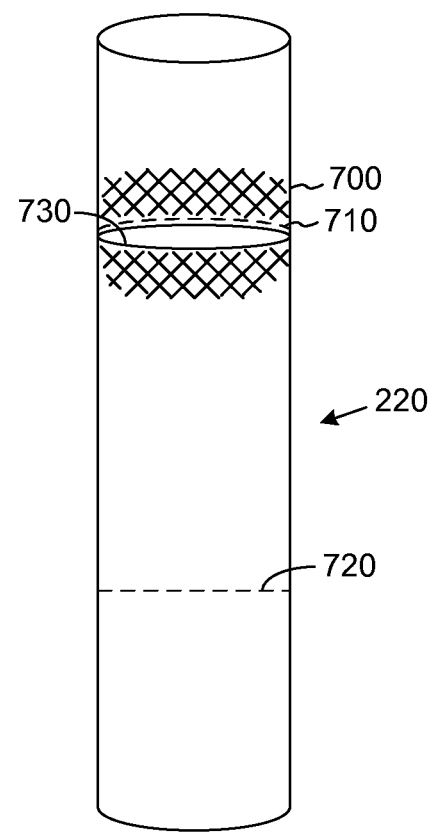
FIG. 7 is a diagram illustrating the manner in which a pocket can be formed in an elongated tubular structure in accordance with one embodiment.

As noted above, the fabric strip may be made of various materials. It should be noted that the term "fabric" is not limited to textiles or woven materials, and should be construed broadly to include any material that can be formed as an elongated, flexible strip. For example, as indicated above, one embodiment utilizes a plastic mesh (e.g., as shown in FIG. 6. This type of mesh is available in a tubular form that is commonly used as a bag to hold melons or other produce, or as a cover to separate and protect bottles. This tubular structure can be conveniently used to form pockets for the drainage reservoirs. For instance, referring to FIG. 7, the tubular mesh 700 can be stitched, tied off or melted together at the upper and lower ends of the pocket location (e.g., at dotted lines 710 and 720) to form an enclosed area within the tubular mesh, and then cutting an opening (730) at the top of the enclosed area to form a pocket. The use of a plastic mesh for the fabric strip may be advantageous in that an embodiment having this construction can be easily cleaned and sanitized by simply putting it in the dishwasher.

Figure 8:
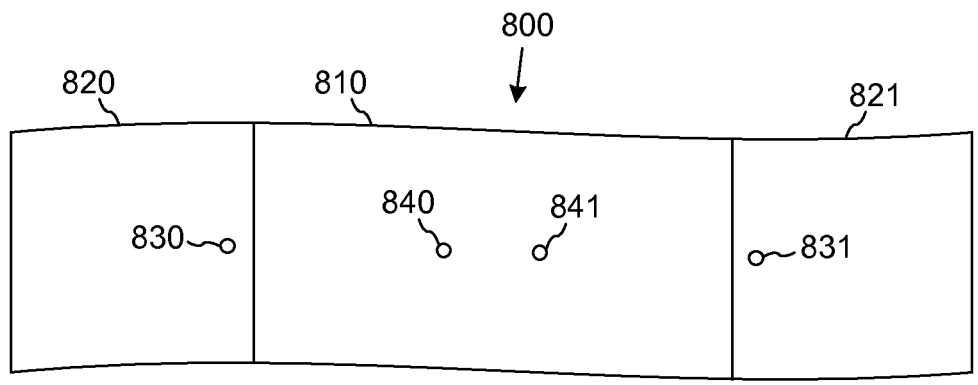
FIG. 8 is a diagram illustrating a plan view of an expansion component in accordance with one embodiment.
Figure 9:
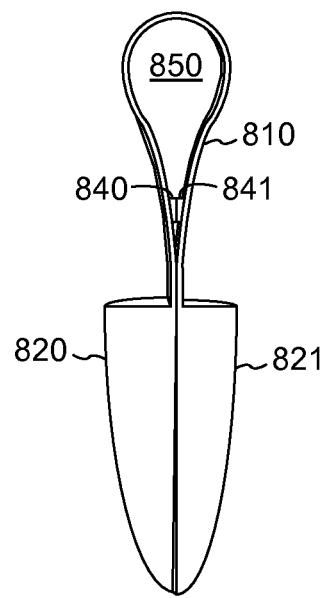
FIG. 9 is a diagram illustrating an expansion component in an installed position in accordance with one embodiment.

In one embodiment, the capabilities of the system can be expanded to include additional pockets/compartments. Referring to FIGS. 8 and 9, an exemplary expansion component is illustrated. FIG. 8 is a diagram illustrating a plan view of the expansion component, while FIG. 9 is a diagram illustrating the expansion component in an installed position.

In the embodiment of FIGS. 8 and 9, FIG. 8 is a diagram illustrating a plan view of the expansion component 800 includes a piece of fabric 810 that has a large pocket (820, 821) at each end. The pockets open toward the center of the FIG. 8 is a diagram illustrating a plan view of the expansion component as shown in FIG. 8. Each pocket has a fastener (830, 831) such as a snap. When large drainage reservoirs are placed in the pockets, the fasteners allow the pockets to be closed, securing the reservoirs. Alternatively, the fasteners can separate one or both of the large pockets into smaller pockets, each of which can hold a small drainage reservoir.

Referring to FIG. 9, expansion component 800 is shown in an installed position. Expansion component 800 can be inserted through the opening or loop at the end of the sash so that each end hangs down on a different side of the opening. Thus, the center of expansion component 800 is supported by the end of the sash. Central fasteners 840 and 841 are connected to each other so that expansion component 800 forms a loop 850 and does not slip out of the opening at the end of the sash. In this position, the openings of pockets 820 and 821 face upward, so reservoirs placed in the pockets will not fall out. As noted above, fasteners 830 and 831 may also be secured to retain the reservoirs in pockets 820 and 821. If expansion component is not needed to support additional drainage reservoirs, it may be removed from the end of the sash, and can instead be installed on a walker, wheelchair arm, bed railing or the like. This is done by simply placing the expansion component over a horizontally extending structure (e.g., the arm of a chair) and connecting the central fasteners to secure the expansion component on the structure. The expansion component can then be used to hold a cell phone, wallet or other such items.

The various embodiments of the present invention may have a number of advantages over conventional means of supporting surgical drains. For instance, because the pocket in which the drainage reservoir is held is secured to the body (e.g., by strap 226), the drainage reservoir cannot swing outward from the body, which could cause the stitches and/or the drainage tube to be pulled from the patient's body. Further, the present device supports the drainage reservoir without requiring the reservoir to be pinned to the patient's clothing, making it more versatile than conventional solutions. The device can be worn either over or under the patient's clothing, or it can be worn without clothing (when the patient is in the shower, for example). The device is compact, lightweight, easy to clean and easy to use. When the device is no longer needed for supporting a surgical drain, it can be used for other purposes. For instance, the device may be worn to provide a pocket for holding a wallet or passport.

The benefits and advantages which may be provided by the present invention have been described above with regard to specific embodiments. These benefits and advantages, and any elements or limitations that may cause them to occur or to become more pronounced are not to be construed as critical, required, or essential features of any or all of the embodiments. As used herein, the terms "comprises," "comprising," or any other variations thereof, are intended to be interpreted as non-exclusively including the elements or limitations which follow those terms. Accordingly, a system, method, or other embodiment that comprises a set of elements is not limited to only those elements, and may include other elements not expressly listed or inherent to the described embodiment.

While the present invention has been described with reference to particular embodiments, it should be understood that the embodiments are illustrative and that the scope of the invention is not limited to these embodiments. Many variations, modifications, additions and improvements to the embodiments described above are possible. It is contemplated that these variations, modifications, additions and improvements fall within the scope of the invention as detailed within the present disclosure.

What is claimed is:

1. A surgical drain support apparatus comprising:
a flexible sash having a first end and a second end, wherein the entire sash comprises a tubular structure;
wherein the sash has an opening which has a closed perimeter at the second end, wherein when the first end is inserted through the opening, and wherein the sash forms an adjustable loop that is adapted to be placed around a first portion of a user's body, thereby supporting the apparatus on the user's body;
wherein the first end of the sash has one or more surgical drain reservoir compartments, wherein each of the compartments is configured to hold a surgical drain reservoir therein;
wherein the sash has a first strap attached thereto, wherein the strap is configured to be wrapped around a second portion of the user's body, wherein the strap holds the first end of the sash against the user's body.

2. The apparatus of claim 1, wherein the sash comprises a piece of fabric.

3. The apparatus of claim 1, wherein the sash comprises a plastic mesh material that is substantially non-absorbent.

4. The apparatus of claim 1, wherein the surgical drain reservoir compartments comprise pockets formed in the tubular structure, wherein one or more of the pockets are formed by, for each of the one or more pockets, sealing the tubular structure to form a lower end of the pocket and forming an opening through one side of the tubular structure to form an upper opening of the pocket.

5. The apparatus of claim 1, further comprising one or more compartment fasteners that are attached to inner walls of one or more of the compartments and are positioned at openings of the one or more of the compartments, wherein the compartment fasteners enable the one or more compartments to be closed, thereby retaining one or more surgical drain reservoirs in the one or more compartments.

6. The apparatus of claim 1, further comprising a plurality of compartment fasteners that are attached to inner walls of at least one large one of the compartments and are positioned to enable the plurality of compartment fasteners to be fastened to each other, thereby enabling the at least one large one of the compartments to be segregated into multiple smaller compartments.

7. The apparatus of claim 1, wherein the opening at the second end comprises a fabric loop that is attached to the second end of the sash.

8. The apparatus of claim 1, further comprising an expansion component, wherein the expansion component comprises one or more additional compartments that are removably attachable to the sash.

9. The apparatus of claim 1, further comprising one or more removable liners positioned within the one or more surgical drain reservoir compartments.

10. A surgical drain support apparatus comprising:
a flexible sash having a first end and a second end;
wherein the sash has an opening which has a closed perimeter at the second end, wherein when the first end is inserted through the opening, and wherein the sash forms an adjustable loop that is adapted to be placed around a first portion of a user's body, thereby supporting the apparatus on the user's body;
wherein the first end of the sash has one or more surgical drain reservoir compartments, wherein each of the compartments is configured to hold a surgical drain reservoir therein;
wherein the sash has a first strap attached thereto, wherein the strap is configured to be wrapped around a second portion of the user's body, wherein the strap holds the first end of the sash against the user's body;
further comprising an expansion component, wherein the expansion component comprises one or more additional compartments that are removably attachable to the sash, wherein the expansion component comprises a piece of fabric and wherein the additional compartments comprise pockets at opposing ends of the piece of fabric, wherein the piece of fabric is positioned through the opening at the second end of the sash.

11. The apparatus of claim 10, further comprising one or more expansion fasteners attached to an intermediate portion of the piece of fabric between the pockets, wherein after the piece of fabric has been positioned through the opening at the second end of the sash, the expansion fasteners are connected to each other, thereby securing the expansion component to the second end of the sash.

12. A method for supporting a surgical drain, the method comprising:
- providing a surgical drain support apparatus, wherein the apparatus includes a flexible sash having a first end and a second end, wherein the first end of the sash has one or more surgical drain reservoir compartments configured to hold one or more surgical drain reservoirs therein, wherein the sash has an opening which has a closed perimeter at the second end, and wherein the first end of the sash has a first strap attached thereto;
- inserting the first end of the sash through the opening in the second end of the sash, thereby forming an adjustable loop;
- placing the adjustable loop around a first portion of a user's body, thereby supporting the apparatus on the user's body;
- wrapping the strap at the first end of the sash around a second portion of the user's body, thereby holding the first end of the sash against the user's body; and
- placing one or more surgical drain reservoirs in the one or more surgical drain reservoir compartments;
- providing an expansion component, wherein the expansion component comprises one or more additional compartments, wherein the expansion component comprises a piece of fabric and wherein the additional compartments comprise pockets at opposing ends of the piece of fabric;
- attaching the expansion component to the sash; and placing one or more additional surgical drain reservoirs in the one or more additional compartments, wherein attaching the expansion component to the sash comprises positioning the piece of fabric through the opening at the second end of the sash and connecting a set of fasteners on the expansion component to each other, thereby securing the expansion component to the second end of the sash.

13. The method of claim 12, further comprising positioning the adjustable loop to support a second portion of the user's body.

14. The method of claim 13, wherein the adjustable loop is positioned to support the user's breast.

\* \* \* \* \*